(12) United States Patent
Keitel

(10) Patent No.: US 10,646,658 B2
(45) Date of Patent: May 12, 2020

(54) INJECTION DEVICE

(71) Applicant: Haselmeier AG, St. Gallen (CH)

(72) Inventor: Joachim Keitel, Esslingen (DE)

(73) Assignee: Haselmeier AG, St. Gallen (CH)

( * ) Notice: Subject to any disclaimer, the term of this patent is extended or adjusted under 35 U.S.C. 154(b) by 185 days.

(21) Appl. No.: 15/942,238

(22) Filed: Mar. 30, 2018

(65) Prior Publication Data

US 2018/0221588 A1    Aug. 9, 2018

Related U.S. Application Data

(63) Continuation of application No. PCT/EP2016/001600, filed on Sep. 26, 2016.

(30) Foreign Application Priority Data

Sep. 30, 2015 (DE) .................... 20 2015 006 841 U

(51) Int. Cl.
  *A61M 5/315* (2006.01)
  *A61M 5/20* (2006.01)
  *A61M 5/31* (2006.01)

(52) U.S. Cl.
  CPC .......... *A61M 5/31553* (2013.01); *A61M 5/20* (2013.01); *A61M 5/2033* (2013.01);
  (Continued)

(58) Field of Classification Search
  CPC .. A61M 5/31553; A61M 5/20; A61M 5/2033; A61M 5/31583; A61M 5/31535;
  (Continued)

(56) References Cited

U.S. PATENT DOCUMENTS

| 5,114,406 A | 5/1992 | Gabriel et al. |
| 5,480,387 A | 1/1996 | Gabriel et al. |

(Continued)

FOREIGN PATENT DOCUMENTS

| DE | 102007013836 A1 | 9/2008 |
| DE | 202012001411 U1 | 5/2013 |

(Continued)

OTHER PUBLICATIONS

International search report dated Jan. 17, 2017 for international application PCT/EP2016/001600 on which this application is based.

(Continued)

*Primary Examiner* — Bradley J Osinski
*Assistant Examiner* — Rachel T. Smith
(74) *Attorney, Agent, or Firm* — Walter Ottesen, P.A.

(57) ABSTRACT

An injection device includes: a housing defining a longitudinal axis; an operating element; a metering member held in the housing so as to be rotatable and fixed in the direction of the axis; the operating element, in a first position for setting a quantity to be dispensed, being mounted so as to be rotatable relative to the housing and rotationally fixedly connected to the metering member via a first coupling; the operating element, in a second position for dispensing, being rotationally fixedly connected to the housing via a second coupling and being rotatable in relation to the metering member; a first latching installation acting between operating element and housing, wherein the first latching installation is effective only in the operating element's first position; and, a second latching installation acting between operating element and metering member, wherein the second latching installation is effective only in the operating element's second position.

16 Claims, 7 Drawing Sheets

(52) U.S. Cl.
CPC .... *A61M 5/31535* (2013.01); *A61M 5/31583* (2013.01); *A61M 5/3157* (2013.01); *A61M 2005/3126* (2013.01); *A61M 2205/581* (2013.01); *A61M 2205/582* (2013.01)

(58) Field of Classification Search
CPC .......... A61M 5/3157; A61M 2205/582; A61M 2205/581; A61M 2005/3126
See application file for complete search history.

(56) References Cited

U.S. PATENT DOCUMENTS

| | | | |
|---|---|---|---|
| 6,221,053 | B1 | 4/2001 | Walters et al. |
| 9,694,136 | B2 | 7/2017 | Keitel et al. |
| 2009/0048561 | A1 | 2/2009 | Burren et al. |
| 2013/0218128 | A1 | 8/2013 | Cowe |
| 2016/0317749 | A1 | 11/2016 | Jugl et al. |
| 2016/0339181 | A1 | 11/2016 | Keitel |
| 2016/0346479 | A1 | 12/2016 | Keitel |
| 2016/0361499 | A1 | 12/2016 | Keitel |
| 2018/0001031 | A1 | 1/2018 | Keitel |
| 2018/0050160 | A1* | 2/2018 | Bilton ............... A61M 5/31553 |
| 2018/0221586 | A1 | 8/2018 | Keitel |
| 2018/0221587 | A1 | 8/2018 | Keitel |
| 2018/0228973 | A1 | 8/2018 | Keitel |

FOREIGN PATENT DOCUMENTS

| | | |
|---|---|---|
| WO | 8907463 A1 | 8/1989 |
| WO | 2004078241 A1 | 9/2004 |
| WO | 2010000085 A1 | 1/2010 |
| WO | 2013117332 A1 | 8/2013 |
| WO | 2014166891 A1 | 10/2014 |
| WO | 2014166900 A1 | 10/2014 |
| WO | 2014166918 A1 | 10/2014 |
| WO | 2015091766 A1 | 6/2016 |

OTHER PUBLICATIONS

International search report dated Jan. 11, 2017 for corresponding international application PCT/EP2016/001599.
International search report dated Feb. 7, 2017 for corresponding international application PCT/EP2016/001597.
International search report dated Dec. 16, 2016 for corresponding international application PCT/EP2016/001598.

* cited by examiner

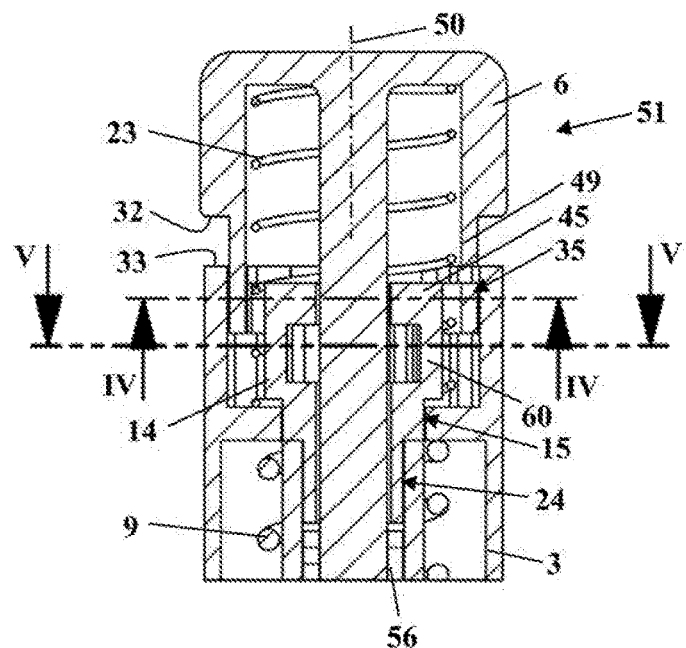
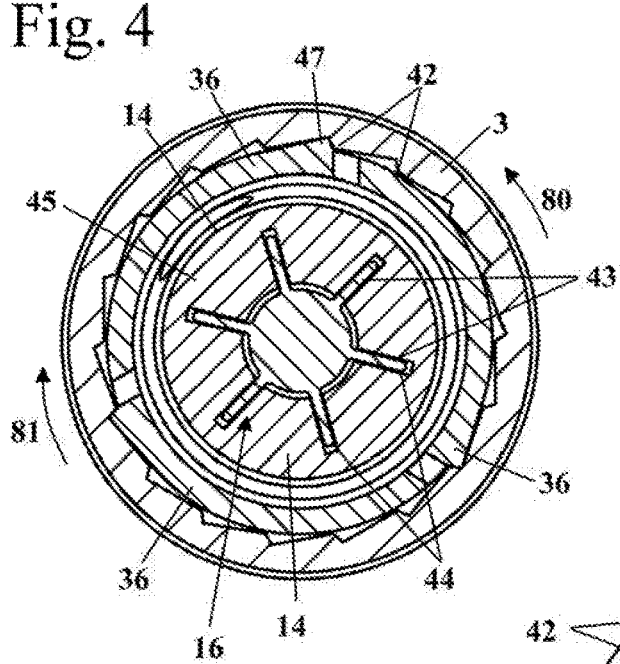
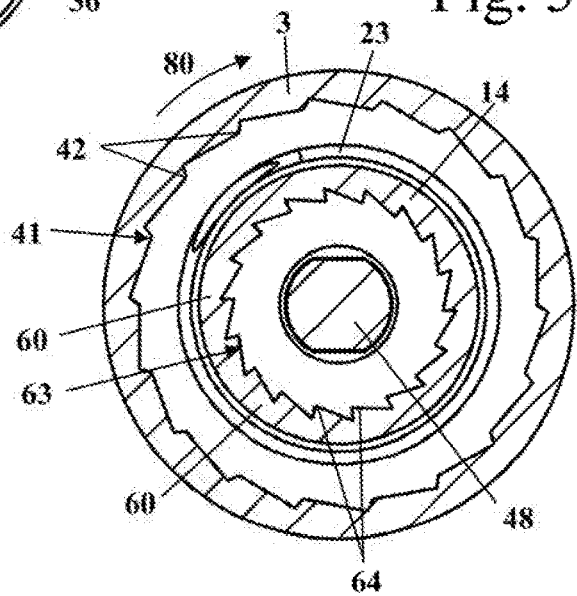

Fig. 6
Fig. 7
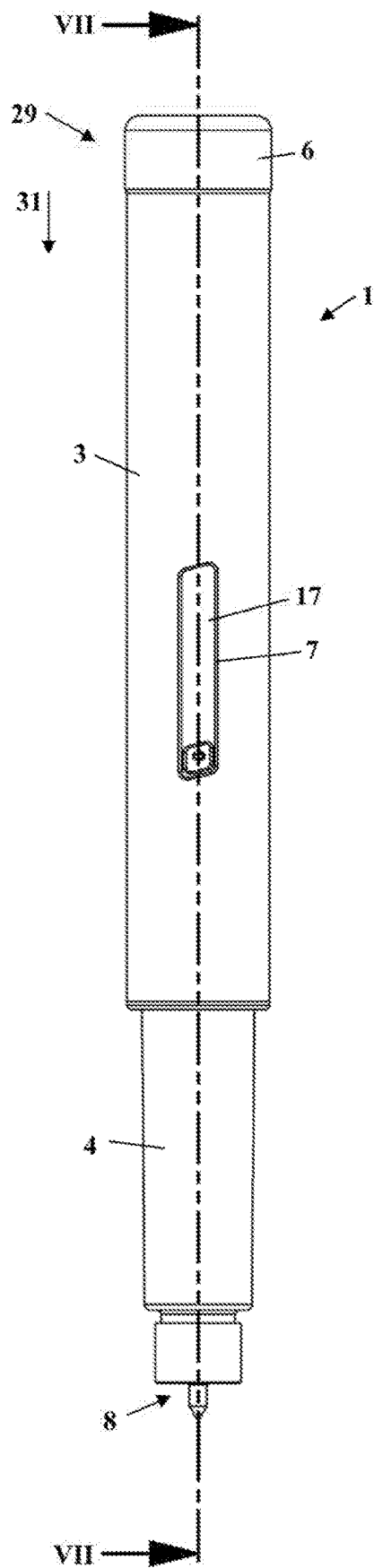
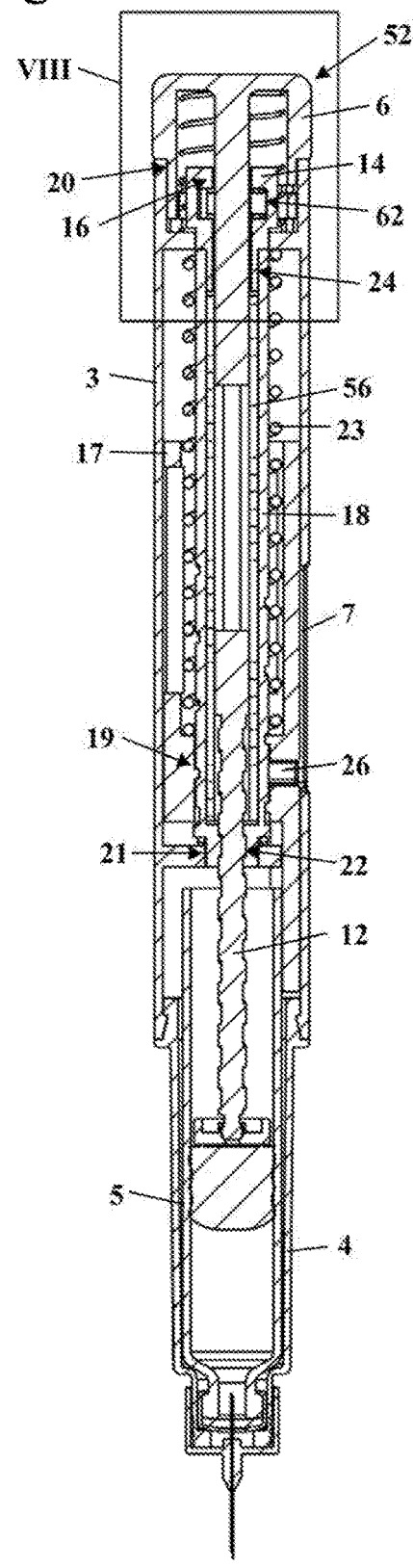

Fig. 11
Fig. 12
Fig. 13
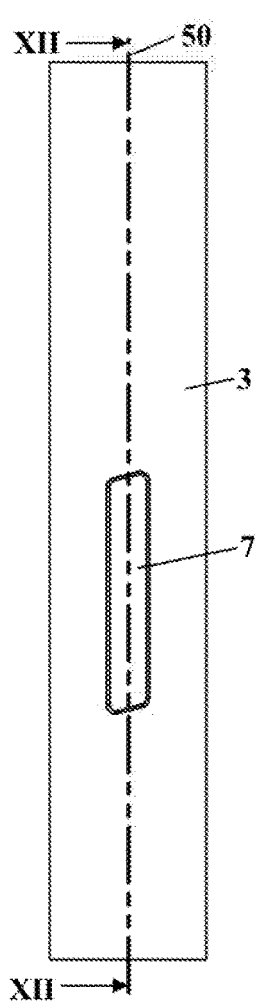
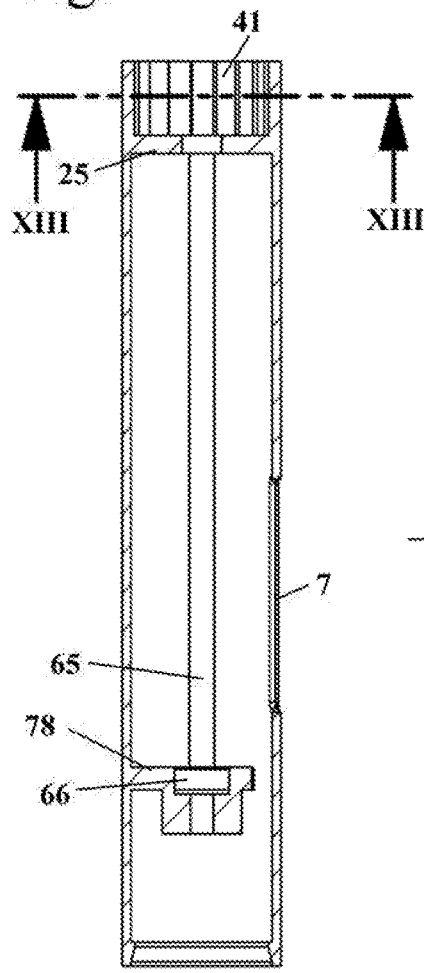
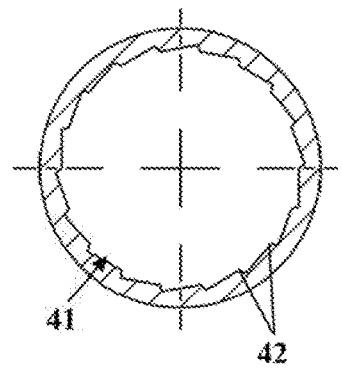
Fig. 14
Fig. 15
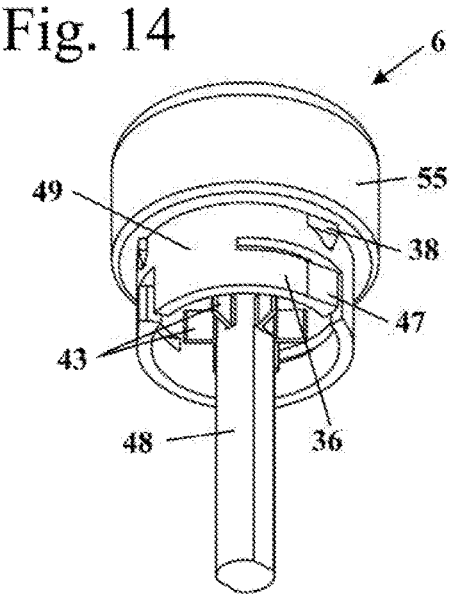
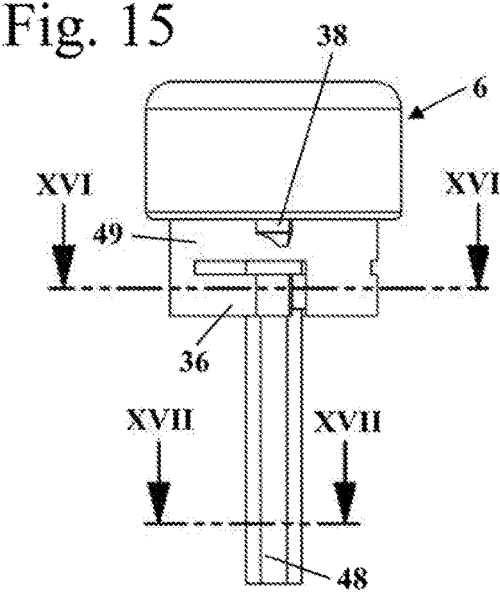

INJECTION DEVICE

CROSS REFERENCE TO RELATED APPLICATIONS

This application is a continuation application of international patent application PCT/EP2016/001600, filed Sep. 26, 2016, designating the United States and claiming priority from German application 20 2015 006 841.3, filed Sep. 30, 2015, and the entire content of both applications is incorporated herein by reference.

BACKGROUND OF THE INVENTION

An injection device of the generic type in which an operating element is rotated in relation to the housing in order for a quantity of injection liquid to be squeezed out to be set is known from DE 20 2012 001 411 U1. A metering member that is rotatably mounted in the housing is conjointly rotated herein. A latching installation acts between the operating element and an injection sleeve that is rotatably mounted in the housing. A second latching insulation acts between the housing and a metering member rotatably mounted in the housing. Both latching installations are effective when setting a quantity of injection liquid to be squeezed out, while only the second latching installation is effective between the housing and the metering member when squeezing out injection liquid. The second latching installation is conceived so as to be comparatively weak, since the operator, when setting a quantity of injection liquid to be squeezed out, has to overcome both latching installations in order for the operating element to be rotated.

SUMMARY OF THE INVENTION

It is an object of the invention to provide an injection device which has a higher level of operating comfort.

This object can, for example, be achieved by an injection device having the features of: a housing; the injection device defining a longitudinal central axis; an operating element; a metering member held in the housing so as to be rotatable and fixed in the direction of the longitudinal central axis; the operating element, in a first position for setting a quantity of injection liquid to be squeezed out, being mounted so as to be rotatable in relation to the housing and being connected in a rotationally fixed manner to the metering member via a first coupling; the operating element, in a second position for squeezing out a quantity of injection liquid to be squeezed out, being connected in a rotationally fixed manner to the housing by way of a second coupling and being rotatable in relation to the metering member; a first latching installation configured to act between the operating element and the housing, wherein the first latching installation is effective only in the first position of the operating element when setting a quantity of injection liquid to be squeezed out; and, a second latching installation configured to act between the operating element and the metering member, wherein the second latching installation is effective only in the second position of the operating element when squeezing out a quantity of injection liquid to be squeezed out.

It is provided that a first latching installation acts in a first position of the operating element, when setting a quantity of injection liquid to be squeezed out. The first latching installation herein acts only in the first position of the operating element. Moreover, a second latching installation which is effective only in a second position of the operating element, when squeezing out a quantity of injection liquid to be squeezed out, is provided between the operating element and the metering member. On account of only one of the two latching installations being effective in each position of the operating element, the latching installations can be conceived so as to be mutually independent. The first latching installation can be conceived in such a way that the operator receives a sufficient haptic and acoustic feedback when setting a quantity of injection liquid to be squeezed out. It can be advantageous for the first latching installation to be conceived such that the operator can also again reduce a once set quantity of injection liquid by rotating the operating element in the opposite direction. The second latching installation can be conceived with a view to the acoustic feedback desired when squeezing out a set quantity of injection liquid. On account of the second latching installation not being active when setting a quantity of injection liquid to be squeezed out, it is possible for the second latching installation to be conceived so as to be comparatively strong such that a clear acoustic feedback is created when squeezing out injection liquid. The two latching installations herein are advantageously configured so as to be completely separate from one another. The latching installations can be conceived so as to be mutually independent.

A latching installation herein is effective when the latching installation, when setting a quantity of injection liquid to be squeezed out, or when squeezing out a quantity of injection liquid to be squeezed out, respectively, thus when the components move relative to one another in the intended manner, provides an acoustic and/or haptic feedback, thus advantageously creates clicking noises, and places the components at predefined relative latching positions. A latching installation is not effective when the components between which the latching installation acts do not move relative to one another in the latching direction such that no latching noises are generated and the elements are adjusted in latching steps.

The metering member, when setting a quantity of injection liquid to be squeezed out, advantageously rotates in a first rotation direction in relation to the housing and, when squeezing out a set quantity of injection liquid, rotates in a second rotation direction, counter to the first rotation direction. The second latching installation is advantageously conceived such that the former permits a rotation of the metering member in relation to the operating element in the second rotation direction, and blocks a rotation of the metering member in relation to the operating element in the first rotation direction. On account thereof, a rotation of the metering member in the first rotation direction is not possible when the operating element is in the second position. The injection device is advantageously an automatically acting injection device in which, upon setting a quantity of injection liquid to be squeezed out, a release element is activated and the injection subsequently is performed automatically. To this end, it is advantageously provided that the injection device has a spring which when setting a quantity of injection liquid to be squeezed out is tensioned, and which in the case of a released first coupling causes injection liquid to be squeezed out.

An advantageous, simple configuration results when the operating element has at least one latching web, wherein the at least one latching web in the first position of the operating element forms part of the first coupling, and in the second position of the operating element forms part of the second latching installation. The latching web thus has a dual function. A simple and compact construction results on account thereof.

The injection device advantageously has an entrainment element which is connected to the metering member in a rotationally fixed manner. The second latching installation is preferably configured on the operating element and on the entrainment element. The first coupling is advantageously also configured on the operating element and on the entrainment element.

A preferred construction of the injection device results when the injection device has a metering piston which is connected in a rotationally fixed manner to the operating element and which by way of a first threaded connection is connected to the metering member. The metering piston is rotated conjointly with the operating element when setting a quantity of injection liquid to be squeezed out. The metering member rotates conjointly with the operating element such that the first threaded connection is ineffective when setting a quantity of injection liquid to be squeezed out. The operating element, and conjointly with the operating element also the metering piston, are guided in a rotationally fixed manner in the housing when squeezing out a quantity of injection liquid to be squeezed out. The first threaded connection, when squeezing out a quantity of injection liquid to be squeezed out, therefore causes an axial movement of the metering piston, this leading to injection liquid being squeezed out.

The injection device advantageously has an injection sleeve which is held in a rotationally fixed manner and so as to be displaceable in the direction of the longitudinal central axis in relation to the housing, and which by way of a second threaded connection is connected to the metering member. When the operating element and thus the metering member are rotated in order for the quantity of injection liquid to be squeezed out to be set, the injection sleeve, by virtue of the second threaded connection and of the rotationally fixed connection to the housing, moves in the distal direction in relation to the housing. During the injection, the injection sleeve is pushed in the proximal direction, thus setting the metering member in rotation. The injection sleeve can therefore advantageously also be utilized for tensioning a spring in the preselection of the dosage, the spring then serving for squeezing out the quantity of injection liquid to be squeezed out. The injection sleeve furthermore advantageously serves for rendering visible to the user a region on the external circumference of the metering member, a scale being depicted on the region. The second threaded connection is conceived such that the injection sleeve in each case displays the set quantity of injection liquid.

BRIEF DESCRIPTION OF THE DRAWINGS

The invention will now be described with reference to the drawings wherein:

FIG. 1 shows a lateral view of an injection device in the zero position;
FIG. 2 shows a section along the line II-II in FIG. 1;
FIG. 3 shows the fragment III from FIG. 2 in an enlarged illustration;
FIG. 4 shows a section along the line IV-IV in FIG. 3;
FIG. 5 shows a section along the line V-V in FIG. 3.
FIG. 6 shows a lateral view of the injection device from FIG. 1 upon squeezing out a set dosage of injection liquid;
FIG. 7 shows a section along the line VII-VII in FIG. 6;
FIG. 11 shows a lateral view of the upper housing part of the injection device;
FIG. 12 shows a section along the line XII-XII in FIG. 11;
FIG. 13 shows a section along the line XIII-XIII in FIG. 12;
FIG. 14 shows a perspective illustration of the operating element of the injection device;
FIG. 15 shows a lateral view of the operating element.

Figure 8:
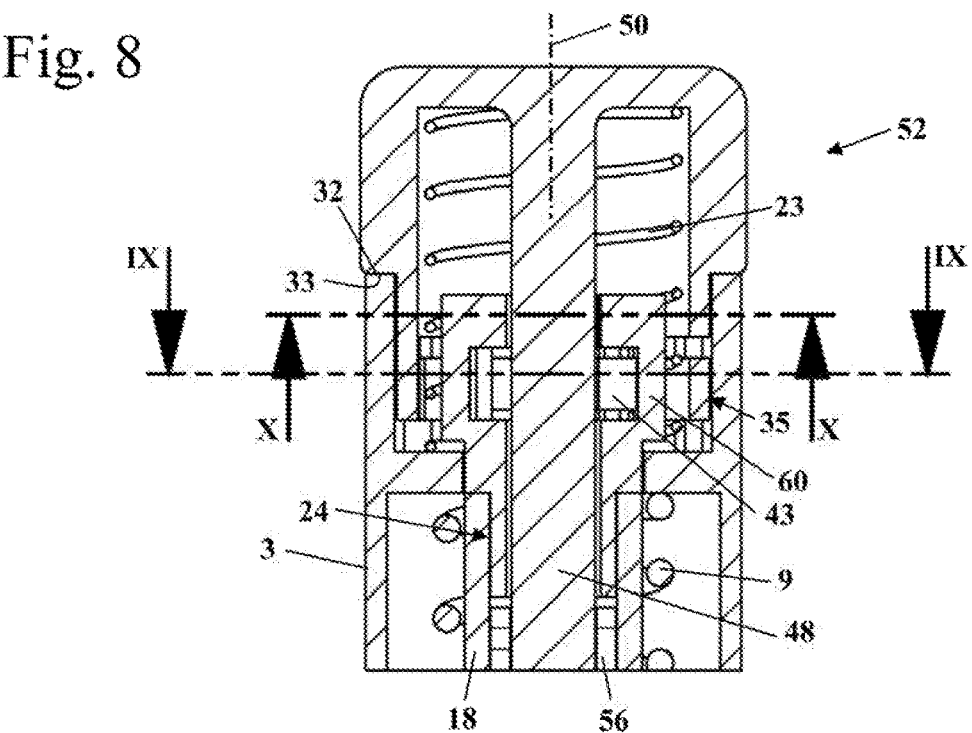
FIG. 8 shows the fragment VIII from FIG. 7 in an enlarged illustration.

DESCRIPTION OF THE PREFERRED
EMBODIMENTS OF THE INVENTION

Figures 1, 2:
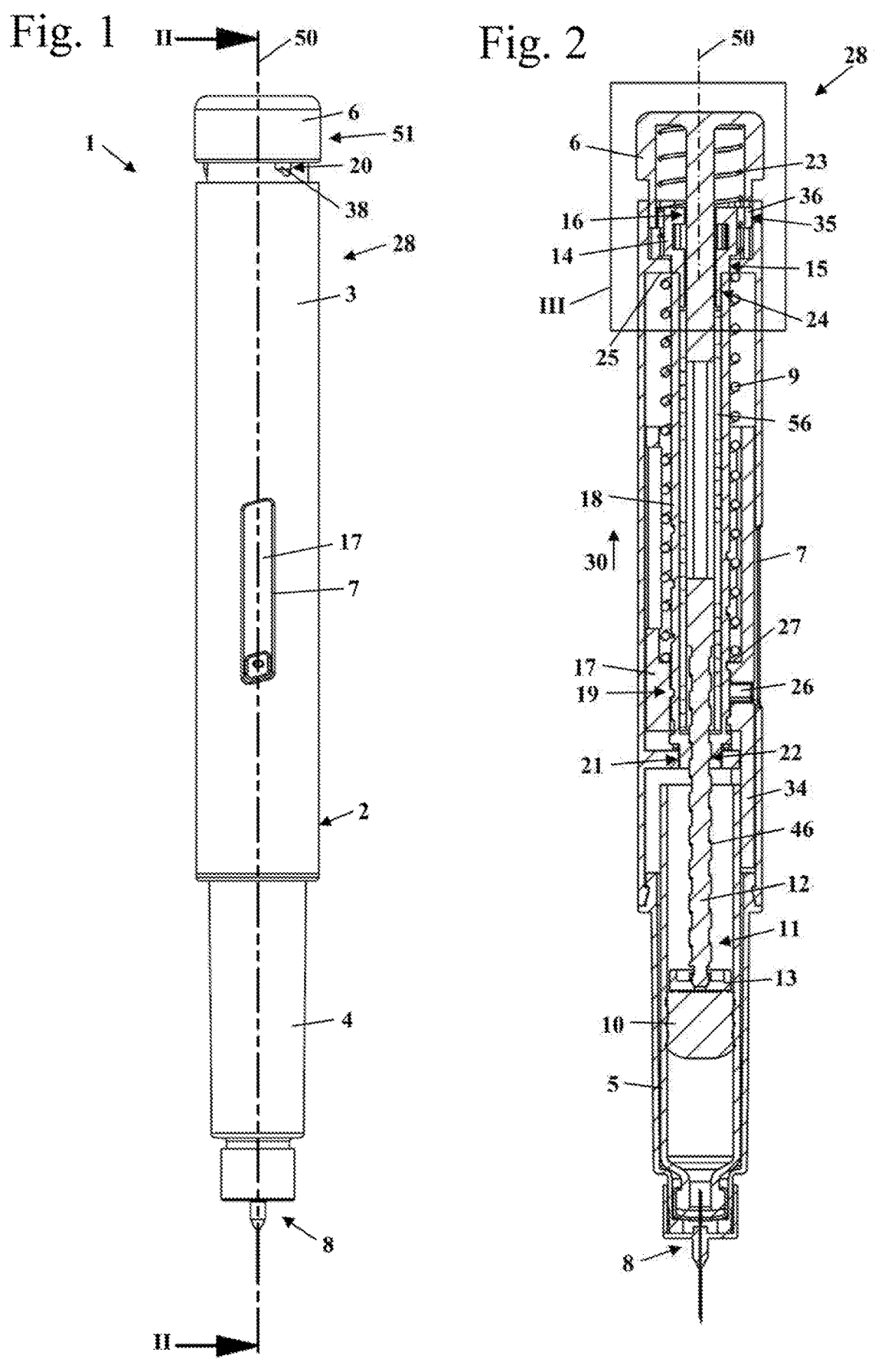

FIG. 1 shows an injection device 1 in a lateral view. The injection device 1 is a mechanical injection device in which the squeezing out of a dosage of injection liquid is performed automatically upon the activation of a release element. The injection device 1 has a housing 2 which comprises an upper housing part 3 and a holder 4 which is secured on an upper housing part 3. The holder 4 is disposed on a proximal side of the upper housing part 3. An injection needle 8 is secured on the proximal side of the holder 4. "Proximal" herein refers to that side of the injection device 1 which in an injection faces the pierced location, and "distal" refers to that side that faces away from the pierced location. The distal end of the injection device 1 is that end that faces away from an injection needle 8 that is held on the injection device 1. The proximal direction describes the injection direction, thus the direction toward the injection needle 8, or the direction in which the injection liquid is squeezed out from a container, respectively. The distal direction describes the opposite direction, thus away from an injection needle 8 that is disposed on the housing 2.

An operating element 6 is disposed on the distal side of the injection device 1. The operating element 6 by way of a coupling 20 is connectable in a rotationally fixed manner to the upper housing part 3. As is shown in FIG. 1, the coupling 20 comprises webs 38, of which one is visible in FIG. 1 and which protrude into a corresponding contour on the upper housing part 3 in order for the operating element 6 to be connected in a rotationally fixed manner to the upper housing part 3. The upper housing part 3 has a viewing window 7 which is advantageously composed of a transparent material such that an injection sleeve 17 that is disposed in the upper housing part 3 is visible through the viewing window 7. The injection device 1 has a longitudinal central axis 50 which runs in the longitudinal direction of the housing 2 of the injection device 1.

FIGS. 1 and 2 show the injection device 1 in a zero position 28 at which no dosage of injection liquid is set. The operating element 6 is in a first, distal position 51 which is the distal terminal position of the operating element 6. As is shown in FIG. 2, a container 5 having an injection liquid is disposed in the holder 4. A plug 10 is disposed in the container 5, a piston disk 13 of a metering piston 11 bearing on the plug 10. The metering piston 11 moreover comprises a piston rod 12 which supports an external thread 46.

The external side of the injection sleeve 17 is visible through the viewing window 7 of the upper housing part 3. The injection sleeve 17 has an opening 26 through which the external circumference of a metering member 18 that is disposed radially within the injection sleeve 17 is visible. The metering member 18, which can also be referred to as a graduated tube, on the external circumference thereof supports a scale 71 (shown in FIG. 24) which is visible to the operator through the viewing window 7 and through the opening 26, and displays the set quantity of injection liquid to be squeezed out.

The metering member 18 is mounted on a pivot bearing 21 so as to be rotatable in the upper housing part 3, and held so as to be axially non-displaceable in the upper housing part 3. The metering member 18 by way of a first threaded connection 22 is connected to the external thread 46 of the piston rod 12. The injection sleeve 17 is held in the upper housing part 3 so as to be displaceable in the direction of the longitudinal central axis 50 and so as to be rotationally fixed in relation to the upper housing part 3. The injection sleeve 17 herein is disposed completely within the housing 2, specifically within the upper housing part 3, in each position of the injection device 1. The metering member 18 and the injection sleeve 17 are interconnected by way of a second threaded connection 19.

An entrainment element 14 is rotatably mounted in the upper housing part 3. The entrainment element 14 is rotatably mounted in a pivot bearing 15 which is configured in the upper housing part 3 and which is formed by a periphery of the upper housing part 3. The entrainment element 14 is connected in a rotationally fixed manner to the metering member 18 by way of a rotationally fixed connection 24. The rotationally fixed connection 24 can be, for example, a press-fit connection or a form-fitting connection.

As is also shown in FIG. 2, a spring 9 which is configured as a compression spring, specifically as a compression coil spring, is disposed in the upper housing part 3. The spring 9 by way of a first end is supported on a bearing periphery 27 of the injection sleeve 17, and by way of the second end thereof is supported on a bearing periphery 25 of the upper housing part 3. The pivot bearing 15 for the entrainment element 14 is also configured on the bearing periphery 25. The spring 9 is disposed so as to be radially outside the metering member 18, and in the zero position 28 shown in FIG. 2, by way of the proximal region of the spring 9, protrudes into an annular space that is formed between the injection sleeve 17 and the metering member 18.

The operating element 6 is connected in a rotationally fixed manner to the piston rod 12 by way of a connection element 56 which in the embodiment is configured as a sleeve. The operating element 6 is supported in relation to the upper housing part 3 by way of a spring 23 which is configured as a compression coil spring. The spring 23 which pushes the operating element 6 in the distal direction, has no influence on the injection rate. The spring 23 is conceived merely such that the operator can move the operating element 6 by way of a comfortable force from the zero position 28 (shown in FIGS. 1 and 2) in the proximal direction. As is shown in FIG. 3, a shoulder 32 is formed on the operating element 6. The upper housing part 3 on the distal end side thereof has a periphery 33. In the case of an operating element 6 that is pushed in the proximal direction, the shoulder 32 interacts with a periphery 33 of the upper housing part 3 and, conjointly with the latter, forms a detent which establishes a proximal position 52 (FIG. 8) of the operating element 6. A further detent which can be configured on the entrainment element 14, for example, is advantageously provided for establishing the distal position 51 of the operating element 6.

A latching installation 35 (FIG. 2) which comprises a plurality of latching arms 36 acts between the operating element 6 and the upper housing part 3. One of the latching arms 36 is visible in FIG. 2. The injection device 1 moreover has a coupling 16 which in the zero position 28 (shown in FIGS. 1 and 2) intercouples the operating element 6 and the entrainment element 14 in a rotationally fixed manner.

In the case of a non-activated operating element 6, the spring 23 pushes the operating element 6 to the first, distal position 51 of the latter. In this position of the operating element 6, the coupling 20 is opened and the operating element 6 is rotatable in relation to the housing 2. In order for a quantity of injection liquid to be squeezed out to be set, the operator rotates the operating element 6 about the longitudinal central axis 50. The entrainment element 14 that by way of the coupling 16 is connected in a rotationally fixed manner to the operating element 6 is conjointly rotated herein. The entrainment element 14 by way of the rotationally fixed connection 24 is connected to the metering member 18 which is likewise conjointly rotated. The piston rod 12 by way of the connection element 56 is connected in a rotationally fixed manner to the operating element 6 and is likewise conjointly rotated. The injection sleeve 17, by virtue of the second threaded connection 19 and of the fixing of the injection sleeve 17 in a rotationally fixed manner in the upper housing part 3, is moved in the distal direction 30 in the rotating movement of the metering member 18. The injection sleeve 17, by way of the bearing periphery 27 thereof, herein moves toward the bearing periphery 25 of the housing 2, on account of which the spring 9 is tensioned. The bearing periphery 25 of the housing 2 herein can form a detent for the distal position of the injection sleeve 17, thus also for the maximum dosage that can be set. The axial position of the operating element 6 is not changed when the dosage of injection liquid to be squeezed out is set. The length of the annular space in which the spring 9 is disposed is shortened by virtue of the movement of the injection sleeve 17 in the distal direction.

FIGS. 3 to 5 show in detail the configuration of the injection device 1 in the region of the operating element 6 and of the distal end of the upper housing part 3. As is shown in FIG. 3, the entrainment element 14 in the distal region thereof has a first portion 45. The operating element 6 has a sleeve portion 49. The proximal region of the sleeve portion 49 protrudes radially between the portion 45 of the entrainment element 14 and the circumferential wall of the upper housing part 3. As is shown in FIG. 4, the circumferential wall of the upper housing part 3 on the internal side thereof has a latching mechanism 41 which is formed by a multiplicity of latching elements 42 that are uniformly distributed on the circumference. The latching arms 36 are disposed on the sleeve portion 49 of the operating element 6. As is shown in FIG. 4, three latching arms 36 are disposed so as to be distributed across the circumference. Each latching arm 36 at the free end thereof supports a latching element 47 which is mounted on the latching arm 36 so as to be sprung in a radially inward manner and which for establishing latching positions of the operating element 6 interacts with the latching elements 42.

In order for a quantity of injection liquid to be squeezed out to be set, the operating element 6 is rotated in a first rotation direction 80 in relation to the upper housing part 3. The first rotation direction 80, when seen in the viewing direction, runs in the proximal direction, that is, from the operating element 6 in the clockwise direction toward the injection needle 8. As is shown in FIGS. 4 and 5, the latching elements 42 are configured so as to be non-symmetrical. On account thereof, any twisting of the operating element 6 in a second rotation direction 81, directed counter to the first rotation direction, is prevented by the first latching installation 35. When twisting the operating element 6 in the first rotation direction 80, the first latching installation 35 generates latching positions that are perceptible and audible to the operator. Any adjustment of the operating element 6 to a position that lies between two latching positions, by virtue of the geometry of the latching elements 42 and 47, and by virtue of the force which by the spring 9 is exerted in the second rotation direction 81 and which resets the operating element 6 to the respectively newest latching position that is assigned to a lower quantity of injection liquid, is not possible.

As is also shown in FIG. 4, the operating element 6 has a series of latching webs 43 which in the embodiment protrude radially outward. In the embodiment, six latching webs 43 which in a sectional illustration perpendicular to the longitudinal central axis 50 are configured as narrow arms that are aligned in the radial direction in relation to the longitudinal central axis 50 are provided. The latching webs 43 in the first, distal position 51 of the operating element 6 (shown in FIGS. 3 to 5) protrude into slot-shaped receptacles 44 in the first portion 45 of the entrainment element 14. The latching webs 43, conjointly with the receptacles 44, form the coupling 16 which connects the operating element 6 in a rotationally fixed manner to the entrainment element 14.

FIG. 5 shows a section through a second portion 60 of the entrainment element 14. The second portion 60 is configured so as to be approximately cylindrical, and is penetrated by a pin portion 48 of the operating element 6. The second portion 60 on the internal wall thereof has a latching mechanism 63 which is formed by a multiplicity of latching elements 64 that are uniformly distributed on the circumference. The function of the latching mechanism 63 will be explained in yet more detail hereunder.

Figure 9:
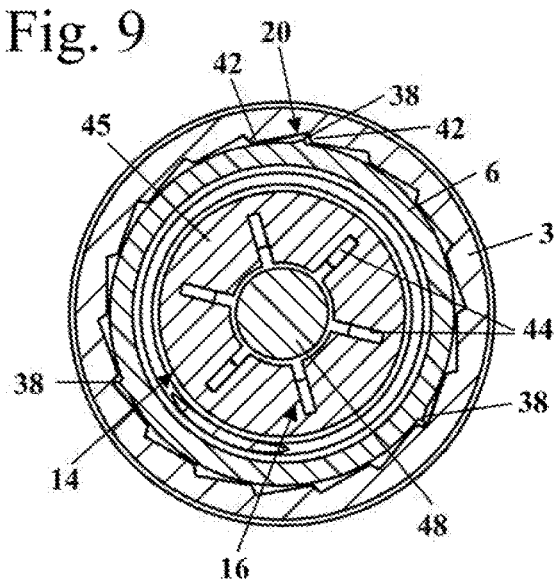
FIG. 9 shows a section along the line IX-IX in FIG. 8.

FIGS. 6 and 7 show the injection device 1 in a terminal position 29, directly upon squeezing out a quantity of injection liquid to be squeezed out. The operating element 6 is in the second, proximal position 52 thereof. The second coupling 20 is closed and connects the operating element 6 in a rotationally fixed manner to the upper housing part 3 such that the operating element 6 cannot rotate in relation to the housing 2. The first coupling 16 is open such that the entrainment element 14 can rotate in relation to the operating element 6. In order for the terminal position 29 to be attained, the operator has moved the operating element 6 from the zero position 28 (shown in FIGS. 1 and 2) in the proximal direction 31, as is indicated in FIG. 6. On account thereof the webs 38 of the coupling 20 have come to engage with the latching elements 42 of the latching installation 35 (FIG. 9). On account thereof, the operating element 6 has been fixed in a rotationally fixed manner in relation to the upper housing part 3. The latching webs 43, by virtue of the movement of the operating element 6 in the proximal direction, have been moved out of the receptacles 44 and the coupling 16, on account thereof, has been released such that the entrainment element 14, conjointly with the metering member 18, has been able to rotate about the longitudinal central axis 50. The rotating movement has been performed by virtue of the axial force that is exerted by the tensioned spring 9 on the injection sleeve 17, the force having caused a rotation of the metering member 18. The rotation has been performed by virtue of the threaded connection 19 and of the injection sleeve 17 being guided in a rotationally fixed manner in the upper housing part 3. The piston rod 12 is connected in a rotationally fixed manner to the upper housing part 3 by way of the connection element 56 and of the operating element 6. The threaded connection 22 therefore causes a movement of the piston rod 12 in the proximal direction 31 when the metering member 18 rotates. On account thereof, the set quantity of injection liquid has been squeezed out from the container 5 until the terminal position 29 (shown in FIGS. 6 and 7) has been reached.

Figure 10:
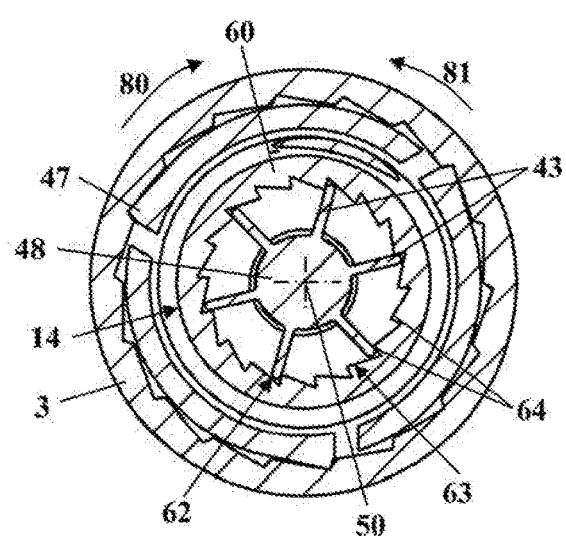
FIG. 10 shows a section along the line X-X in FIG. 8.

FIGS. 8 to 10 show in detail the coupling 20 and a second latching installation 62. As is shown in FIG. 9, a total of three webs 38 which protrude between latching elements 42 of the upper housing part 3 and, on account thereof, connect the operating element 6 in a rotationally fixed manner to the upper housing part 3 are provided. As is also shown in FIG. 9, the latching webs 43 have moved out of the receptacles 44 in the entrainment element 14 such that the first coupling 16 is opened, permitting a relative rotation of the entrainment element 14 in relation to the operating element 6.

As is shown in FIG. 10, the latching webs 43 in the terminal position 29 are disposed in the region of the latching mechanism 63 having the latching elements 64, and conjointly with the latter form the second latching installation 62. The latching webs 43 thus form both part of the coupling 16 as well as part of the latching installation 62. The latching elements 64 of the latching mechanism 63 are also configured so as to be non-symmetrical, and permit a rotation of the entrainment element 14 in the second rotation direction 81 in relation to the operating element 6. A rotation of the entrainment element 14 in the first rotation direction 80 in relation to the operating element 6 is prevented by virtue of the alignment of the latching flanks so as to be approximately radial in relation to the longitudinal central axis 50.

The first latching installation 35 determines the intensity of the latching steps that are perceptible and audible when setting a quantity of injection liquid to be squeezed out. The second latching installation 62 is not effective when setting the quantity of injection liquid to be squeezed out, since the latching webs 43 are not located in the region of the latching mechanism 63. Rather, the operating element 6 and the entrainment element 14 are interconnected in a rotationally fixed manner by way of the latching webs 43. In order for an injection to be released, the operating element 6 is moved by the operator from the distal position 51 to the proximal position 52. On account thereof, the operating element 6 when squeezing out injection liquid is located in the second proximal position 52. The first latching installation 35 is not effective in this position, since the coupling 20 connects the operating element in a rotationally fixed manner to the upper housing part 3. The coupling 16 between the operating element 6 and the entrainment element 14 is released. The second latching installation 62 is active. The second latching installation 62 establishes the intensity of the perceptible and audible latching steps when squeezing out a quantity of injection liquid to be squeezed out. On account of the two latching installations 35 and 62 being configured so as to be mutually separate, and of in each case only one of the two latching installations 35 or 62 being effective, the intensity of the latching steps when setting a quantity of injection liquid to be squeezed out, and when squeezing out injection liquid, can be conceived so as to be mutually independent. In principle, the number of latching steps can also be dissimilar.

By virtue of the force stored in the spring 9, the injection is performed automatically once the coupling 16 has been released. The spring 9 herein is conceived such that the force stored in the spring 9 is sufficient in order for the resistance of the plug 10 and the resistance exerted by the second latching installation 62, to be overcome and for injection liquid to be squeezed out from the container 5.

FIGS. 11 to 13 show in detail the configuration of the upper housing part 3. The viewing window 7 which extends so as to be parallel with the longitudinal central axis 50 is shown in FIG. 11. As is shown in FIG. 12, the upper housing part 3 at the distal end thereof, on the internal circumference, has the latching mechanism 41, as is also shown in FIG. 13. As is shown in FIG. 12, the latching mechanism 41 in the embodiment extends up to the bearing periphery 25 which runs perpendicularly in relation to the longitudinal central axis 50 and which serves for mounting the entrainment element 14, the spring 9 being supported on the bearing periphery 25. The upper housing part 3 has a transverse wall 78 on which the metering member 18 is supported. The transverse wall 78 has a bearing opening 66 in which the metering member 18 is rotatably mounted. Guide webs 65 in which the injection sleeve 17 is guided so as to be axially displaceable and rotationally fixed in relation to the upper housing part 3 are provided on the internal side of the upper housing part 3.

FIGS. 14 to 17 show in detail the configuration of the operating element 6. The operating element 6 has an operating portion 55 which protrudes from the housing 2 and at which the operator when setting a quantity of injection liquid to be squeezed out can rotate the operating element 6 in relation to the upper housing part 3. The sleeve portion 49 which on the external side thereof supports the webs 38 of the coupling 20, and the latching arms 36 of the first latching installation 35, is disposed on the proximal side of the operating portion 55. The sleeve portion 49 is penetrated by the pin portion 48. The latching webs 43 are disposed within the sleeve portion 49 on the pin portion 48.

Figure 16:
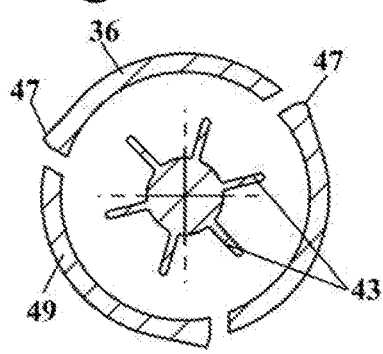
FIG. 16 shows a section along the line XVI-XVI in FIG. 15.
Figure 17:
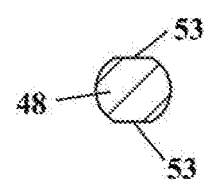
FIG. 17 shows a section along the line XVII-XVII in FIG. 15.
Figure 18:
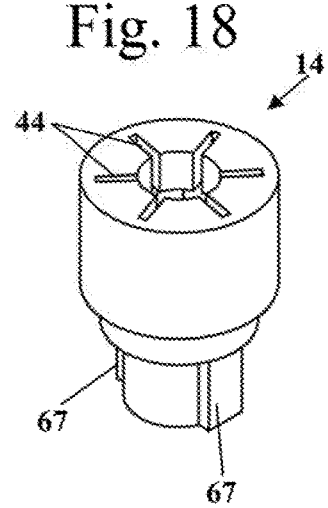
FIGS. 18 and 19 show perspective illustrations of an entrainment element of the injection device.
Figure 19:
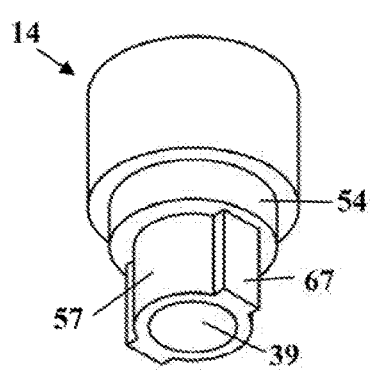
Figure 20:
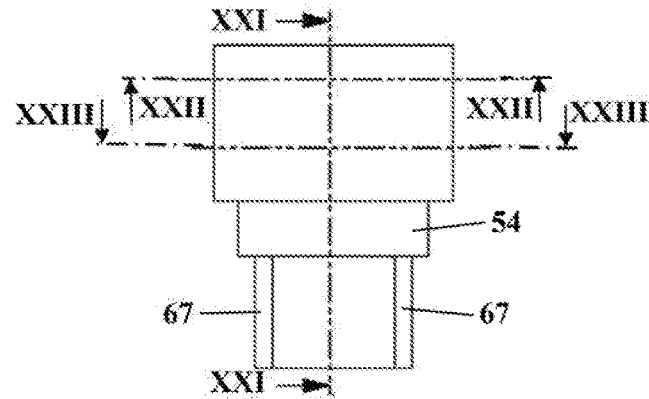
FIG. 20 shows a lateral view of the entrainment element from FIGS. 18 and 19.

FIG. 16 shows the arrangement of the latching webs 43 within the sleeve portion 49. As is shown in FIG. 17, the pin portion 48 on the external side thereof has two mutually opposite bevels 53 which serve for the rotationally fixed connection to the connection element 56 (FIG. 2).

FIGS. 18 to 23 show in detail the entrainment element 14. The entrainment element 14 has a bearing portion 54 by way of which the former is rotatably mounted on the bearing periphery 25. The entrainment element 14, on the proximal side of the bearing portion 54, has a sleeve portion 57, securing webs 67 which run so as to be parallel with the longitudinal central axis 50 being provided on the external side of the sleeve portion 57. The securing webs 67 serve for connecting the entrainment element 14 in a rotationally fixed manner to the metering member 18. The entrainment element 14 has a continuous opening 39, the pin portion 48 of the operating element 6 protruding through the opening 39, as is shown in FIG. 8.

Figure 21:
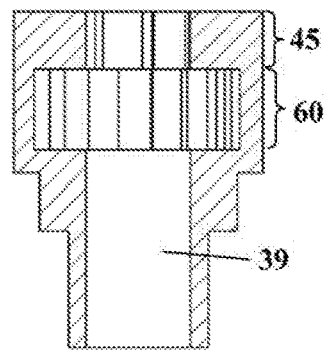
FIG. 21 shows a section along the line XXI-XXI in FIG. 20.
Figure 22:
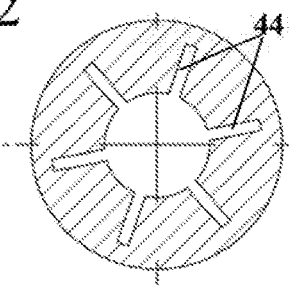
FIG. 22 shows a section along the line XXII-XXII in FIG. 20.
Figure 23:
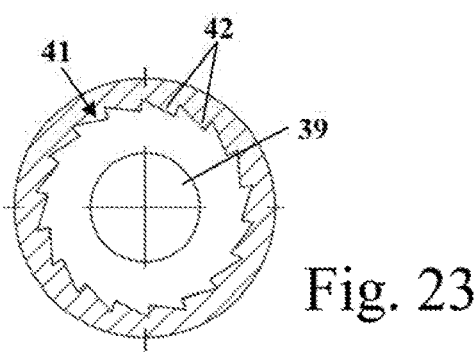
FIG. 23 shows a section along the line XXIII-XXIII in FIG. 20.

As is shown in FIGS. 21 to 23, the entrainment element 14 has the first portion 45 in which the receptacles 44 of the coupling 16 are configured, and the second portion 60 in which the latching mechanism 41 having the latching elements 42 is disposed. The second portion 60 herein is disposed on the proximal side of the first portion 45.

Figure 24:
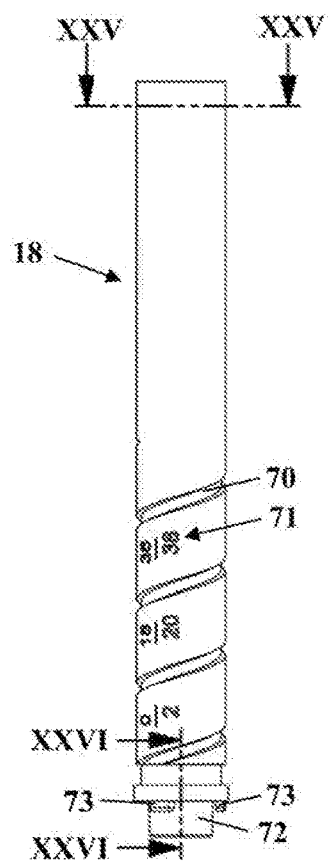
FIG. 24 shows a lateral view of the metering member of the injection device.
Figure 25:
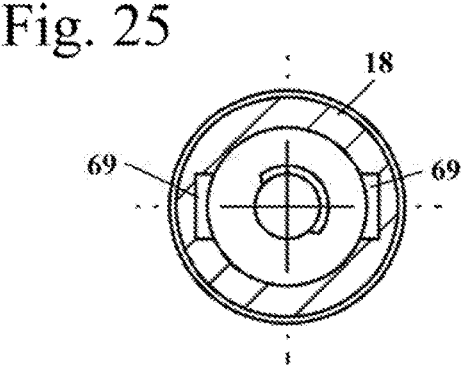
FIG. 25 shows a section along the line XXV-XXV in FIG. 24.
Figure 26:
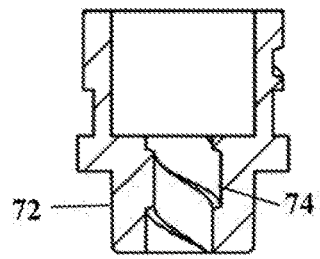
FIG. 26 shows a section along the line XXVI-XXVI in FIG. 24.

FIGS. 24 to 26 show in detail the metering member 18. The metering member 18 on the proximal side thereof has a bearing connector 72 by way of which the metering member 18 is mounted in the bearing opening 66 of the upper housing part 3. Bearing webs 73 which at the end side bear on the transverse wall 78 of the upper housing part 3 and which reduce the friction between the metering member 18 and the upper housing part 3 are provided so as to be adjacent to the bearing connector 72. The scale 71 is applied on the external circumference of the metering member 18. The metering member 18 in the region of the scale 71 has an external thread 70 which interacts with an internal thread 77 (shown in FIG. 28) of the injection sleeve 17 and conjointly with the latter forms the threaded connection 19.

As is shown in FIG. 25, the metering member 18 at the distal end thereof has two depressions 69 into which the securing webs 67 of the entrainment element 14 (FIG. 19) protrude in order for the entrainment element 14 to be connected in a rotationally fixed manner to the metering member 18. As is shown in FIG. 26, the metering member 18 on the bearing connector 72 has an internal thread 74 which interacts with the external thread 46 of the piston rod 12 and conjointly with the latter forms the threaded connection 22.

Figure 27:
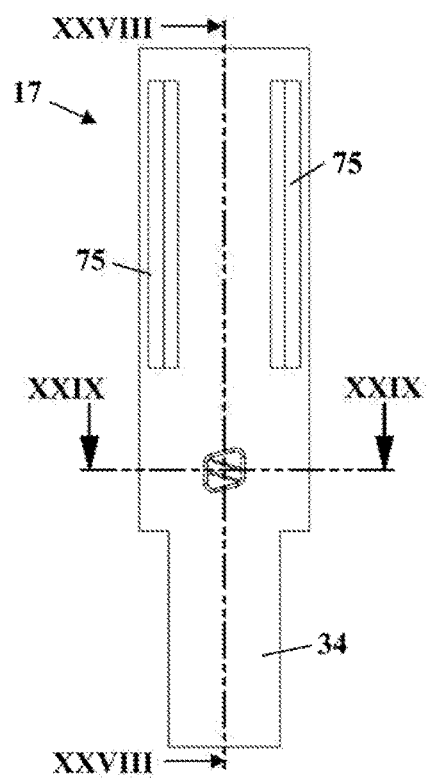
FIG. 27 shows a lateral view of the injection sleeve of the injection device.
Figure 28:
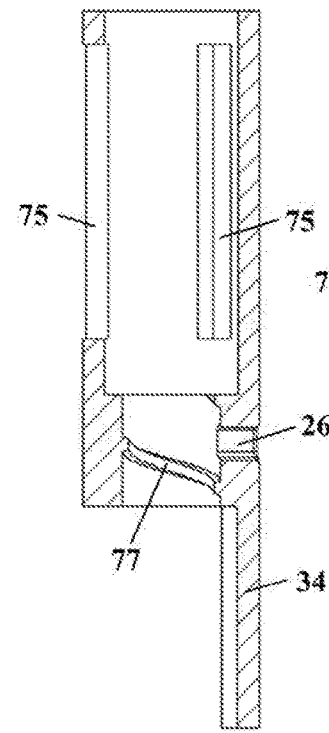
FIG. 28 shows a section along the line XXVIII-XXVIII in FIG. 27; and,
FIG. 29 shows a section along the line XXIX-XXIX in FIG. 27.
Figure 29:
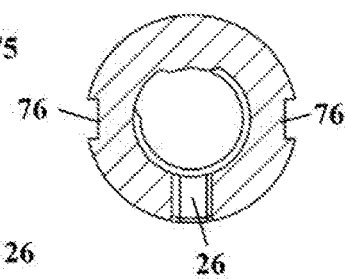

FIGS. 27 to 29 show in detail the injection sleeve 17. The injection sleeve 17 has clearances 75 which run in the direction of the longitudinal central axis 50 and serve for reducing the weight. As is shown in FIG. 28, the injection sleeve 17 has a web 34 which protrudes in the proximal direction. The web 34 in the distal position of the injection sleeve 17 covers the proximal part of the scale 71. As is also shown in FIG. 28, the opening 26 is disposed in the region of the internal thread 77.

As is shown in FIG. 29, the injection sleeve 17 on the external circumference thereof has guide grooves 76 which serve for the rotationally fixed connection to the upper housing part 3, the guide webs 65 of the upper housing part 3 protruding into the guide grooves 76.

The present invention can also be advantageous in the case of a manual injection device, thus in the case of an injection device in which the injection liquid is squeezed out by the operator by pushing onto the operating element 6. In the case of such an injection device, an operating element 6 and an entrainment element 14 which, when setting a quantity of injection liquid to be squeezed out, are in a first axial mutual relative position, and when squeezing out the injection liquid are in a second mutual axial position can also be provided. In one preferred configuration embodiment, the second latching installation has a spur gearing which is disposed on the end side of the entrainment element and which interacts with the arms of the operating element 6 that in the direction of the longitudinal central axis 50 protrude toward the entrainment element. Such a latching installation is effective or ineffective, depending on the mutual relative position of the operating element and of the entrainment element. It is advantageously provided that the latching installation in the first, distal position of the operating element does not engage with the spur gearing, and on account thereof is not effective. In the second, proximal position of the operating element, the at least one arm advantageously engages with the spur gearing such that the latching installation in this relative position is effective. The latching installation herein is advantageously conceived such that a rotation of the entrainment element in relation to the operating element is possible only in one direction. The latching installation thus has the function of a free-wheeling unit.

Other configuration embodiments of the latching installation can also be advantageous.

It is understood that the foregoing description is that of the preferred embodiments of the invention and that various changes and modifications may be made thereto without departing from the spirit and scope of the invention as defined in the appended claims.

What is claimed is:

1. An injection device comprising:
a housing defining a longitudinal central axis;
an operating element;
a metering member held in said housing so as to be rotatable and fixed in a direction of the longitudinal central axis;
said operating element, in a first position for setting a quantity of injection liquid to be squeezed out, being mounted so as to be rotatable in relation to said housing and being connected in a rotationally fixed manner to said metering member via a first coupling;
said operating element, in a second position for squeezing out the quantity of injection liquid to be squeezed out, being connected in a rotationally fixed manner to said housing by way of a second coupling and being rotatable in relation to said metering member;
a first latching installation configured to act between said operating element and said housing, wherein said first latching installation is effective only in the first position of said operating element when setting the quantity of injection liquid to be squeezed out;
a second latching installation configured to act between said operating element and said metering member, wherein said second latching installation is effective only in the second position of the operating element when squeezing out the quantity of injection liquid to be squeezed out; and,
a metering piston connected in a rotationally fixed manner to said operating element, where said metering piston is connected to said metering member by way of a first threaded connection.

2. The injection device of claim 1, wherein said metering member, when setting the quantity of injection liquid to be squeezed out, rotates in a first rotation direction in relation to the housing, and, when squeezing out a set quantity of injection liquid, rotates in a second rotation direction counter to said first rotation direction in relation to the housing.

3. The injection device of claim 2, wherein said second latching installation permits a rotation of said metering member in relation to said operating element in said second rotation direction, and blocks a rotation of the metering member in relation to the operating element in the first rotation direction.

4. The injection device of claim 1, further comprising a spring which is tensioned when setting the quantity of injection liquid to be squeezed out and which, when said first coupling is released, causes injection liquid to be squeezed out.

5. The injection device of claim 1, wherein:
said operating element has at least one latching web; and, said at least one latching web, in the first position of the operating element, forms part of the first coupling and, in the second position of the operating element, forms part of the second latching installation.

6. The injection device of claim 1 further comprising an entrainment element connected to said metering member in a rotationally fixed manner.

7. The injection device of claim 6, wherein said second latching installation is formed on said operating element and on said entrainment element.

8. The injection device of claim 6, wherein said first coupling is formed on said operating element and on said entrainment element.

9. The injection device of claim 7, wherein said first coupling is formed on said operating element and on said entrainment element.

10. The injection device of claim 1 further comprising an injection sleeve held in a rotationally fixed manner and so as to be displaceable in the direction of the longitudinal central axis in relation to the housing; and, said injection sleeve being connected to said metering member by way of a second threaded connection.

11. The injection device of claim 1 further comprising an injection sleeve held in a rotationally fixed manner and so as to be displaceable in the direction of the longitudinal central axis in relation to the housing; and, said injection sleeve being connected to said metering member by way of a second threaded connection.

12. An injection device comprising:
a housing defining a longitudinal central axis;
an operating element;
a metering member held in said housing so as to be rotatable and fixed in a direction of the longitudinal central axis;
said operating element, in a first position for setting a quantity of injection liquid to be squeezed out, being mounted so as to be rotatable in relation to said housing and being connected in a rotationally fixed manner to said metering member via a first coupling;
said operating element, in a second position for squeezing out the quantity of injection liquid to be squeezed out, being connected in a rotationally fixed manner to said housing by way of a second coupling and being rotatable in relation to said metering member;
a first latching installation configured to act between said operating element and said housing, wherein said first latching installation is effective only in the first position of said operating element when setting the quantity of injection liquid to be squeezed out;
a second latching installation configured to act between said operating element and said metering member, wherein said second latching installation is effective only in the second position of the operating element when squeezing out the quantity of injection liquid to be squeezed out; and,
a spring which is tensioned when setting the quantity of injection liquid to be squeezed out and which, when said first coupling is released, causes injection liquid to be squeezed out.

13. An injection device comprising:
a housing defining a longitudinal central axis;
an operating element;
a metering member held in said housing so as to be rotatable and fixed in a direction of the longitudinal central axis;
said operating element, in a first position for setting a quantity of injection liquid to be squeezed out, being mounted so as to be rotatable in relation to said housing and being connected in a rotationally fixed manner to said metering member via a first coupling;

said operating element, in a second position for squeezing out the quantity of injection liquid to be squeezed out, being connected in a rotationally fixed manner to said housing by way of a second coupling and being rotatable in relation to said metering member;

a first latching installation configured to act between said operating element and said housing, wherein said first latching installation is effective only in the first position of said operating element when setting the quantity of injection liquid to be squeezed out;

a second latching installation configured to act between said operating element and said metering member, wherein said second latching installation is effective only in the second position of the operating element when squeezing out the quantity of injection liquid to be squeezed out; and, an entrainment element connected to said metering member in a rotationally fixed manner.

14. The injection device of claim 13, wherein said second latching installation is formed on said operating element and on said entrainment element.

15. The injection device of claim 13, wherein said first coupling is formed on said operating element and on said entrainment element.

16. The injection device of claim 14, wherein said first coupling is formed on said operating element and on said entrainment element.

* * * * *